United States Patent [19]

Ray

[11] 4,218,535
[45] Aug. 19, 1980

[54] DETERMINATION OF ENZYME SUBSTRATE CONCENTRATION

[75] Inventor: Robert A. Ray, Fullerton, Calif.

[73] Assignee: Beckman Instruments, Inc., Fullerton, Calif.

[21] Appl. No.: 967,324

[22] Filed: Dec. 7, 1978

Related U.S. Application Data

[63] Continuation of Ser. No. 667,330, Mar. 16, 1976, abandoned.

[51] Int. Cl.² .................. G01N 31/14; C07G 7/02
[52] U.S. Cl. .................................. 435/12; 435/14; 435/25; 435/183; 435/188; 435/189; 435/195; 435/227
[58] Field of Search ............. 195/103.5 R, 103.5 C, 195/99; 435/12, 14, 25, 183, 188, 190, 195, 227

[56] References Cited

U.S. PATENT DOCUMENTS 3,977,944  8/1976  Müller-Matthesius et al. ... 195/103.5 R

FOREIGN PATENT DOCUMENTS 2349819  4/1975  Fed. Rep. of Germany.

OTHER PUBLICATIONS

Dixon et al., Enzymes. Academic Press Inc., N.Y., 1958 (pp. 171–181).

Zöllner et al., Heparin, Methods of Enzymatic Analysis, Academic Press, N.Y., 1965 (pp. 79–83).
Fritz et al., Protease Inhibitors, Methods of Enzymatic Analysis, Academic Press, Inc. N.Y., 1974 (pp. 1064–1068 and 1085).

*Primary Examiner*—David M. Naff
*Attorney, Agent, or Firm*—R. J. Steinmeyer; Robert R. Meads; Robert S. Frieman

[57] ABSTRACT

An enzymatic reagent is provided for use in the kinetic measurement of the concentration of an enzyme substrate present in a sample and possessing the Michaelis-Menten relationship between reaction rate and substrate concentration. The reagent includes an enzyme such as glucose oxidase, uricase or urease for reacting with corresponding enzyme substrates such as glucose, uric acid or urea. In addition, the reagent includes a non-reacting competitive inhibitor of the enzyme. The inhibitor is present in an amount sufficient to improve the linearity of the reaction rate-concentration relationship associated with the enzyme substrate reaction at concentrations which are low relative to the Michaelis-Menten constant, $K_m$, for the particular enzyme substrate reaction. The improved linearity, in turn, improves the accuracy of the kinetic measurements of substrate concentration made by linear output analyzers especially in an upper portion of the predetermined range where the relationship is particularly nonlinear.

19 Claims, 3 Drawing Figures

DETERMINATION OF ENZYME SUBSTRATE CONCENTRATION

This is a continuation of application Ser. No. 667,330, filed Mar. 16, 1976, now abandoned.

BACKGROUND OF THE INVENTION

Field of Invention

The present invention relates to the chemical analysis of biological substances to determine the chemical composition thereof and more particularly to an enzymatic reagent for use in the kinetic measurement of enzyme substrates, hereinafter referred to simply as "substrates," present in biological samples and possessing a relationship between reaction rate and substrate concentration defined by the Michaelis-Menten equation.

Description of Prior Art

Within the field of the present invention it is a common procedure to determine the concentration of substrates such as glucose in blood or urine since the concentration of glucose in body fluids is indicative of the operation of various fundamental body functions. Another common procedure is to determine the concentration of the substrate urea in blood serum since the concentration of urea is indicative of the operation of the kidneys.

Various methods and apparatus have been employed in the past to determine the concentration of such enzyme substrates present in biological test samples. One such method involves the monitoring of the rate of change of certain characteristics associated with the chemical reaction of an enzyme and the enzyme substrate present in the biological test sample. U.S. Pat. No. 3,857,771 to James C. Sternberg for Rate Sensing Batch Analyzer and U.S. Pat. No. 3,765,841 to Gerald R. Paulson and Robert A. Ray for Method and Apparatus for Chemical Analysis describe such methods and analyzers useful in such methods. More particularly, the foregoing patents describe methods and analyzers for determining the concentration of an enzyme substrate such as glucose or urea in blood serum. As described in said patents, when a serum sample is introduced into a reagent, the serum reacts therewith causing a continuing change in a characteristic of the reagent-sample mixture. The analyzer includes a sensor for monitoring the characteristic of the reagent-sample mixture and for generating a first electrical output signal directly proportional thereto. A differentiator circuit is provided for producig a second electrical signal. The second signal is the time derivative of the first signal and is a measure of the rate of change of the characteristic of the mixture. The time derivative signal is directly proportional to the concentration of the enzyme substrate in the sample as long as the concentration does not exceed the level corresponding to about 0.05 Km, where Km is the Michaelis-Menten constant of the Michaelis-Menten equation as set forth hereinbelow.

It has been found, however, that as the concentration of the enzyme substrate present in the mixture increases to levels approaching Km, there is a reduction in the accuracy with which the time derivative signal from linear output analyzers, such as the Sternberg and Paulson-Ray analyzers, indicates substrate concentration. This is due to the nonlinear Michaelis-Menten relationship between substrate concentration and reaction rate associated with all enzyme-substrate reactions which is defined by the Michaelis-Menten equation expressed as follows:

$$V = \frac{V_{max}[S]}{K_m + [S]}$$

wherein:
[S] = substrate concentration
V = the observed reaction velocity at a given substrate concentration [S]
Km = Michaelis constant expressed in units of concentration
Vm = maximum reaction velocity at saturating concentration of substrate.

BRIEF DESCRIPTION OF THE DRAWINGS

The Michaelis-Menten equation which is also referred to as the Michaelis-Menten relationship is better understood by reference to FIGS. 1 and 2. In FIG. 1, the relationship between reaction rate and substrate concentration is illustrated by the Michaelis-Menten curve 1. The value of [S] corresponding to the half-maximal velocity is designated Km which is a constant that is a fundamental characteristic of every enzyme. In analyzers of the type described by the aforesaid Sternberg and Paulson-Ray patents, the concentration of the unknown substrate measured in the reaction mixture is dependent on the concentration of substrate in the physiological fluid of interest and on the dilution ratio of the fluid to the enzymatic reagent. The actual unknown concentration of the substrate in the reaction mixture falls somewhere on curve 1 representative of the enzyme in question.

In FIG. 2, the unknown concentration of substrate falls in a range between zero and S'. The velocities corresponding to the substrate concentration in such a range follow the hyperbolic curve 2. A straight line is the desired relationship between the output signal of the instrument and the unknown substrate concentration. However, the line OA in FIG. 2 is only an approximation of a straight line. Thus, it is possible to improve the linearity of the curve OA by going to smaller unknown concentrations, and line OB in FIG. 2 corresponding to the substrate concentration range 0 to S" is a closer approximation to a straight line. Unfortunately, going to smaller substrate concentrations also reduces the velocity and thus the output signal of the analyzer. Until the invention provided for herein, this seemingly unalterable property of enzyme systems limited the linearity of enzyme-substrate reactions and the use of the aforesaid analyzers.

SUMMARY OF THE INVENTION

It has been discovered that the aforesaid analyzers may be used to more accurately determine the concentration of substrates having a Michaelis-Menten relationship between substrate concentration and reaction rate thereof if a nonreacting competitive inhibitor of the enzyme used to promote the reaction with the substrate is added thereto in amounts to cause the Km to increase to a larger value or an "apparent Km" defined by the expression:

$$Km = \frac{Vm\ [S]}{Km\ [1\ +\ Ki(I)]\ +\ [S]}$$

wherein Ki is the inhibition constant for the competitive inhibitor as defined in standard texts on enzyme kinetics, I is the inhibitor concentration, and the other symbols in the Km equation correspond to the definitions given in connection with the Michaelis-Menten equation. From the above expression it should be appreciated that the effect of the nonreacting competitive inhibitor of the present invention is to obtain a more linear relationship between substrate concentration and reaction rate inasmuch as the apparent Km is now larger relative to the substrate concentration.

Figure 1:
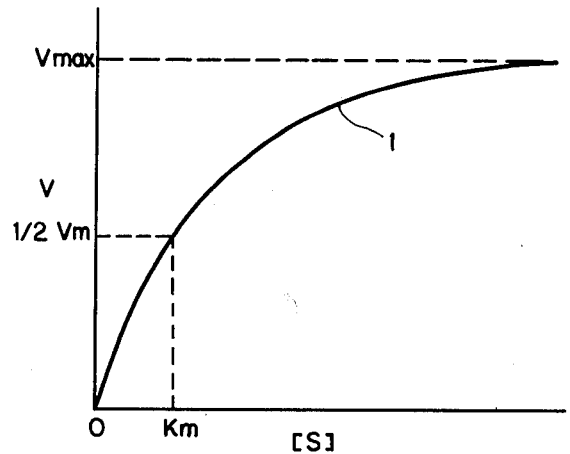
FIG. 1 is a plot of the Michaelis-Menten curve for the reaction rate of enzyme catalyzed reactions.
Figure 2:
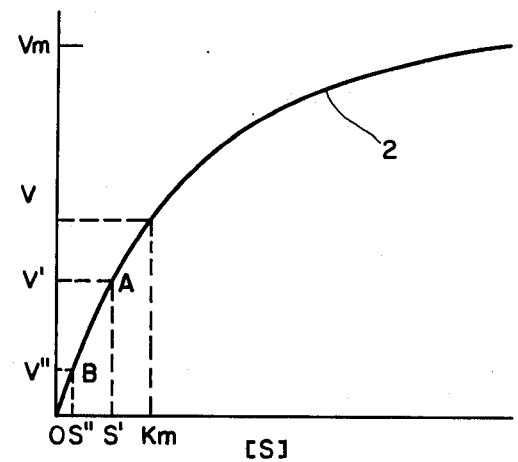
FIG. 2 is a plot of a Michaelis-Menten curve for the reaction rate of enzyme catalyzed reactions wherein two ranges of substrate concentration, S' and S", are compared.
Figure 3:
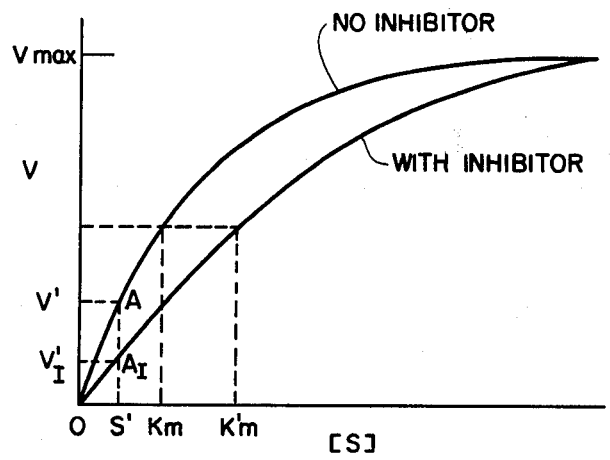
FIG. 3 is a comparative plot of the Michaelis-Menten curve for an enzyme catalyst reaction without and with an inhibitor of the present invention.

Referring to FIG. 3, the Michaelis-Menten curve for an enzyme in the presence and in the absence of a competitive inhibitor is shown. The inhibitor has the effect of raising the apparent Km to a higher levelr than in the absence of an inhibitor, and as a result, if the substrate concentration range 0 to S' is the same, then the curve $OA_1$ is more nearly a straight line than is curve OA. Such a condition is confirmed by the calculations set forth in Tables 1, 2, 3, and 4 wherein the values for Vm and Km are arbitrarily selected and set forth in the tables, and the values of S are chosen from 0 to 10. The resultant value for V may be calculated.

In Tables 1 to 4, $$V = \frac{V\mathrm{max}\ [S]}{Km\ +\ [S]}.$$

and $V' = M[S]$ where M is a straight-line slope constant associated with the linear analyzer. For example, if an analyzer of the aforesaid Sternberg or Paulson-Ray type is calculated to provide an output response of 20 for a sample having a concentration $[S] = 5$, then when $[S] = 3$ it would be expected that the output response would be 12 ($V' = M[S]$). However, from the Michaelis-Menten equation the actual response will be 13 which is higher than 12 and is thus nonlinear. The percent error (% error) in Tables 1 to 4 is the percent deviation of V from V', e.g., for $[S] = 3$ in Table 1, the result will be 13, a 8.25% increase over the desired linear response of 12 which is not obtained.

In Table 1, when the data for [S] and V are fitted to a straight line determined by 0 and the mid scale point, $[S] = 5$, the actual curve (Column V) is seen to be 16.7% low at $[S] = 10$ and 8.25% high at $[S] = 3$ compared to the straight line (Column $V^1$). The $[S] = 5$ point corresponds to a calibration point for a linear analyzer of the Sternberg or Paulson-Ray type. When Km decreases and the S range is held constant, the deviation from linearity increases very significantly as indicated in Table 2. In contrast, when Km has been increased, the linearity improves as indicated in Table 3. Finally, when the enzyme activity is increased to compensate for the lower absolute rates as by increasing Vm from 100 to 180, the deviation from linearity remains essentially unchanged as illustrated in Table 4. As a result, by adding nonreacting competitive inhibitors to enzyme reagents, the effective Km of the enzymes can be raised and thereby improve the linearity of the response of Sternberg or Paulson-type analyzers.

An additional advantage of the present invention is that samples of specimen may now contain the same inhibitor as the enzyme to levels of 100 fold greater than the level in the enzyme for the sample volumes of 10 microliters added to 1000 microliters of reagent and 20 fold for samples of volumes of 50 microliters added to 1000 microliters of reagent.

DESCRIPTION OF A PREFERRED EMBODIMENT

The embodiments of the invention provided for herein are described in terms of specific substrates but it is to be understood that the invention is not limited thereto but comprehends any nonreacting competitive inhibitor of the particular enzyme or enzymes used to assay for a specific substrate concentration having a Michaelis-Menten relationship between substrate concentration and the reaction rate thereof. Such inhibitors are generally, but without limitation thereto, structural analogs of the specific substrate which compete with the substrate for the active site on the enzyme to reduce the catalytic activity thereof.

GLUCOSE ASSAY

In assaying for the substrate glucose with a reagent comprising the enzyme glucose oxidase, the nonreacting competitive inhibitor added to said reagent is selected from the group consisting of D-glucal and gluconic acid. The concentrations of said inhibitors will vary depending on the particular formulation of the reagent and may be determined empirically by one skilled in the art having the benefit of the invention disclosed herein. However, about a 0.1 M solution of D-glucal or from about 15 mM to about 50 mM of gluconic acid may be used with the specific reagent for a glucose assay as set forth in Example 1.

EXAMPLE 1

A specific reagent for a glucose assay to which is added one of the inhibitors described above, comprises about 150 International Units per milliliter of glucose oxidase derived from *A. niger*, about 5 weight percent of denatured alcohol, about $10^{-2}$ M of potassium iodide, catalase and ammonium molybdate as catalysts, a mixture of 0.1 M soduim and potassium mono and dihydrophosphate until a pH of 6 is achieved, and about $5 \times 10^{-4}$ M of iodine.

URIC ACID ASSAY

In assaying for the substrate uric acid with a reagent comprisig the enzyme uricase, the nonreacting competitive inhibitor added to said reagent is selected from a group consisting of xanthine and hypoxanthine. The concentrations of said inhibitors will vary depending upon the particular formuation of the reagent and may be determined empirically by one skilled in the art having the benefit of the invention disclosed herein.

However, from about $10^{-5}$ to about $10^{-3}$ M and preferably about $10^{-4}$ M solution of xanthine may be used with the specific reagent for a uric acid assay described in Example 2.

EXAMPLE 2

A specific reagent for a uric acid assay to which is added one of the inhibitors described above and in a desired concentration set forth therein, comprises about 0.1 M of sodium tetraborate and about 0.25 International Units per milliliter of uricase.

UREA ASSAY

In assaying for the substrate urea with a reagent comprising the enzyme urease, the nonreacting competitive inhibitor added to said reagent is selected from the group consisting of suramin or thiourea. The concentrations of said inhibitor will vary depending upon the particular formulation of the reagent and may be determined empirically by one skilled in the art having the benefit of the invention disclosed herein. A specific reagent for a urea assay is described in Example 3.

EXAMPLE 3

A specific reagent for a urea assay comprises about 35 to about 45 International Units of Jackbean urease, about 2 to about 5 millimolar of tris-(hydroxymethyl) aminomethane, about 0.2 millimolar of ethylenediaminetetraacetic acid (disodium salt) in about 5 millimolar of N-2-hydroxyethylpiperazine-N'-2-ethane sulfonic acid, and about 0.01 millimolar of butyl paraben.

While the embodiments of the invention chosen herein for purposes of the disclosure are considered to be preferred, the invention is intended to cover all changes and modifications of the disclosed embodiments which fall within the spirit and scope of the invention.

I claim:

1. An enzymatic reagent for kinetically measuring with a linear output analyzer the concentration of glucose having a Michaelis-Menten relationship between concentration of glucose and the reaction rate thereof and a known value for Km forming a part of said relationship, said reagent comprising about 150 International Units per milliliter of glucose oxidase, about 5% by weight of denatured alcohol, about $10^{-2}$ M of potassium iodide, catalase and ammonium molybdate as catalysts, a mixture of sodium and potassium mono and dihydrogenphosphate to a pH of about 6, and about $5 \times 10^{-4}$ M of iodine, and a nonreacting competitive inhibitor of glucose oxidase in an amount sufficient to increase the value of Km relative to said glucose concentration and thereby increase the linearity of the output response of said linear analyzer at values of concentration below Km.

2. An enzymatic reagent as set forth in claim 1 wherein said inhibitor comprises D-glucal in a concentration of about 0.1 M.

3. An enzymatic reagent as set forth in claim 1 wherein said inhibitor comprises gluconic acid in a concentration of about 15 to about 50 millimolar.

4. An enzymatic reagent for kinetically measuring with a linear output analyzer the concentration of uric acid having a Michaelis-Menten relationship between said uric acid concentration and the reaction rate thereof and a known value for Km forming a part of said relationship, said reagent comprising about 0.1 M of sodium tetraborate and about 0.25 International Units per milliliter of uricase and a nonreacting competitive inhibitor of uricase in an amount sufficient to increase the value of Km relative to said uric acid concentration and thereby increase the linearity of the output response of said linear analyzer at values of concentration below Km.

5. An enzymatic reagent as set forth in claim 4 wherein said inhibitor comprises about $10^{-5}$ to about $10^{-3}$ M of xanthine.

6. An enzymatic reagent as set forth in claim 4 wherein said inhibitor comprises hypoxanthine.

7. An enzymatic reagent for kinetically measuring with a linear output analyzer the concentration of urea having a Michaelis-Menten relationship between said urea concentration and the reaction rate thereof and a known value for Km forming a part of said relationship, said reagent comprising about 35 to about 45 International Units of Jackbean urease, about 2 to about 5 millimolar of tris-(hydroxymethyl) aminomethane, about 0.2 millimolar of ethylenediaminetetraacetic acid (disodium salt) in about 5 millimolar of N-2-hydroxyethylpiperazine-N'-2-ethane sulfonic acid and about 0.01 millimolar of butyl paraben, and a nonreacting competitive inhibitor of urease in an amount sufficient to increase the value of Km relative to said urea concentration and thereby increase the linearity of the output response of said linear analyzer at values of concentration below Km.

8. An enzymatic reagent as set forth in claim 7 wherein said inhibitor comprises suramin.

9. An enzymatic reagent as set forth in claim 7 wherein said inhibitor comprises thiourea.

10. In a method for kinetically measuring enzyme substrate concentrations with linear output analyzers which monitor a rate of reaction between an enzyme present in a sample and a reagent comprising an enzyme for reacting with said substrate present in the sample, said reaction between said enzyme and said substrate possessing a Michaelis-Menten relationship between reaction rate and substrate concentration and a known value for Km forming a part of said relationship, the improvement consisting of the step of adding to said sample or reagent a nonreacting competitive inhibitor of said enzyme in an amount sufficient to increase the value of Km relative to said substrate concentration to increase the linearity of said reaction rate-substrate concentration relationship, whereby the accuracy of the kinetic measurement of substrate concentration with linear output analyzers is improved.

11. The method of claim 10 wherein said enzyme is glucose oxidase.

12. The method of claim 10 wherein said enzyme is glucose oxidase and said inhibitor is D-glucal.

13. The method of claim 10 wherein said enzyme is glucose oxidase and said inhibitor is gluconic acid.

14. The method of claim 10 wherein said enzyme is uricase.

15. The method of claim 10 wherein said enzyme is uricase and said inhibitor is xanthine.

16. The method of claim 10 wherein said enzyme is uricase and said inhibitor is hypoxanthine.

17. The method of claim 10 wherein said enzyme is urease.

18. The method of claim 10 wherein said enzyme is urease and said inhibitor is suramin.

19. The method of claim 10 wherein said enzyme is urease and said inhibitor is thiourea.

* * * * *